United States Patent
Jee et al.

(10) Patent No.: US 7,186,577 B2
(45) Date of Patent: Mar. 6, 2007

(54) METHOD FOR MONITORING A DENSITY PROFILE OF IMPURITIES

(75) Inventors: Yun-Jung Jee, Yongin-si (KR); Sun-Yong Choi, Sungnam-si (KR); Chung-Sam Jun, Suwon-si (KR); Kwan-Woo Ryu, Suwon-si (KR)

(73) Assignee: Samsung Electronics Co. Ltd., Suwon-si (KR)

( * ) Notice: Subject to any disclaimer, the term of this patent is extended or adjusted under 35 U.S.C. 154(b) by 141 days.

(21) Appl. No.: 10/787,772

(22) Filed: Feb. 27, 2004

(65) Prior Publication Data

US 2004/0253750 A1    Dec. 16, 2004

(30) Foreign Application Priority Data

Feb. 27, 2003    (KR) ............ 10-2003-0012425

(51) Int. Cl.
*H01L 21/66* (2006.01)
(52) U.S. Cl. .............. 438/16; 438/748; 438/514; 257/E21.53
(58) Field of Classification Search ............ 438/14, 438/16, 7, 8, 748, 514; 356/445, 432; 257/E21.53
See application file for complete search history.

(56) References Cited

U.S. PATENT DOCUMENTS

| | | | | |
|---|---|---|---|---|
| 4,479,848 A | * | 10/1984 | Otsubo et al. | 438/16 |
| 4,795,260 A | * | 1/1989 | Schuur et al. | 356/400 |
| 5,074,669 A | * | 12/1991 | Opsal | 356/445 |
| 5,185,273 A | * | 2/1993 | Jasper | 438/5 |
| 5,229,304 A | * | 7/1993 | Chang et al. | 438/7 |
| 5,497,407 A | | 3/1996 | Komatsu et al. | |
| 5,520,769 A | * | 5/1996 | Barrett et al. | 438/14 |
| 5,652,151 A | * | 7/1997 | Asada | 438/18 |
| 5,796,113 A | * | 8/1998 | Nagli et al. | 250/483.1 |
| 6,121,060 A | * | 9/2000 | Kameyama | 438/14 |
| 6,506,615 B2 | * | 1/2003 | Chen et al. | 438/14 |
| 6,900,894 B2 | * | 5/2005 | McMillen et al. | 356/445 |

FOREIGN PATENT DOCUMENTS

JP    10-325786    12/1998

OTHER PUBLICATIONS

Wolf, "Silicon Processing for the VLSI Era," vol. 1, 1986, pp. 189-191, 532-534.*

* cited by examiner

*Primary Examiner*—Bradley K. Smith
*Assistant Examiner*—Steven J. Fulk
(74) *Attorney, Agent, or Firm*—Lee & Morse, P.C.

(57) ABSTRACT

A method of monitoring a density profile of impurities, the method including presetting a monitoring position of a thin layer coated on a substrate, the density profile of impurities being monitored from the monitoring position in a direction of thickness of the thin layer, moving an exposer for exposing a local area of the thin layer to the monitoring position, exposing the local area of the thin layer along the direction of thickness of the thin layer, forming a shape profile of the exposed local area of the thin layer, and monitoring the density profile of impurities by determining a density of impurities in accordance with the shape profile, and an apparatus therefor. The impurity density profile may be monitored without destroying a substrate on which a thin layer is coated, and an amount of impurities used for forming the thin layer may be monitored and controlled in real-time.

20 Claims, 5 Drawing Sheets

METHOD FOR MONITORING A DENSITY PROFILE OF IMPURITIES

BACKGROUND OF THE INVENTION

1. Field of the Invention

The present invention relates to a method and an apparatus for monitoring a density profile of impurities. More particularly, the present invention relates to a method and an apparatus for monitoring a density profile of boron (B) or phosphorous (P) in an insulating interlayer of the semiconductor substrate.

2. Description of the Related Art

Technological trends of high integration degree and operation speed of recent semiconductor devices render intervals between various patterns in a memory cell shorter, so that a space between gate electrodes becomes narrower and a conductive pattern forming a gate electrode becomes higher. Therefore, coating an insulating interlayer to planarize a substrate surface frequently causes a void defect between two adjacent gate electrodes.

A borophosphorous silicate glass (hereinafter, referred to as BPSG) is now widely used as an insulating interlayer to prevent a void defect since BPSG has good fluidity and step coverage. The BPSG includes small doses of boron (B) and phosphorous (P) in a silicon oxide ($SiO_2$) layer, and is generally deposited on a substrate surface through an atmospheric pressure chemical vapor deposition (APCVD) process. Accordingly, an operation characteristic of a BPSG layer is decisively influenced by the density of boron (B) and phosphorous (P). More specifically, the density profile of the boron (B) and phosphorous (P) distributed along a depth of a cross sectional surface of a BPSG layer (hereinafter, referred to as "depth profile") has more effect on operation characteristics of the BPSG layer than does the bulk density of the boron (B) and phosphorous (P).

When relatively small quantities of the boron (B) and phosphorous (P) in a lower portion of the BPSG layer are used, a void defect is more frequently generated and a static refresh rate is considerably reduced during a self-aligned contact process. In addition, an etching rate is strongly influenced by the densities of the boron (B) and phosphorous (P) Therefore, the cross sectional surface of the BPSG layer becomes non-uniform in accordance with the density profiles of the boron (B) and phosphorous (P).

In general, the density profile of boron (B) or phosphorous (P) has been measured by a secondary ion mass spectrometry (SIMS) method or a glow discharge luminescence spectrometry (GDLS) method. However, the SIMS and GDLS methods are carried out after destruction of the BPSG layer. Furthermore, a density analysis method using a Fourier transform infra-red (FT-IR) apparatus indicates the bulk density of boron (B) and phosphorous (P), but does not indicate any information regarding density variation along a thickness of the BPSG layer.

Therefore, there is a need for an improved density analysis method for analyzing a depth profile of boron (B) and phosphorous (P) in real time during the process without destruction the substrate.

SUMMARY OF THE INVENTION

Accordingly, the present invention is directed to a method of monitoring a depth profile of impurity densities in a pattern of a semiconductor substrate without destruction of the substrate during the process. Furthermore, the present invention is directed to an apparatus for monitoring a depth profile of impurity densities in a pattern of a semiconductor substrate without destruction of the substrate during the process.

Therefore, it is a feature of an embodiment of the present invention to provide a method of monitoring a density profile of impurities, the method including presetting a monitoring position of a thin layer coated on a substrate, the density profile of impurities being monitored from the monitoring position in a direction of thickness of the thin layer, moving an exposer for exposing a local area of the thin layer to the monitoring position, exposing the local area of the thin layer along the direction of thickness of the thin layer, forming a shape profile of the exposed local area of the thin layer, and monitoring the density profile of impurities by determining a density of impurities in accordance with the shape profile.

The thin layer preferably includes an insulating interlayer coated on a semiconductor substrate.

The insulating interlayer preferably includes a borophosphorous silicate glass (BPSG) layer.

Exposing the local area of the thin layer along the direction of thickness of the thin layer may include a wet etching process.

The wet etching process may be carried out using a buffer oxide etchant (BOE).

Forming the shape profile may include irradiating a light onto the exposed local area of the thin layer, detecting an intensity of light reflected from the exposed local area of the thin layer, and comparing the intensity of the light reflected from adjacent reflecting points of the exposed local area.

Forming the shape profile may further may include transforming the shape profile into an image.

Transforming the shape profile into an image may include using a solid state imaging device.

Therefore, it is another feature of an embodiment of the present invention to provide an apparatus for monitoring a density profile of impurities, the apparatus including a stage on which a substrate is disposed, a thin layer including a plurality of impurities being coated on the substrate, an exposer that exposes a local area of the thin layer along a direction of thickness of the thin layer, a shape profile generator that generates a shape profile of the exposed local area of the thin layer, a density profile generator that generates a density profile of impurities by determining a density of the impurities corresponding to the shape profile, and a controller that controls the exposer, the shape profile generator, and the density profile generator by using a preset monitoring position of the thin layer, the density profile of impurities being monitored from the preset monitoring position in the direction of thickness of the thin layer.

The exposer preferably includes a container for containing an exposing material and a nozzle for injecting the exposing material into the local area of the thin layer.

The container preferably includes a tube containing an etchant for performing a wet etching process, and the nozzle preferably includes a micro pipette for injecting the etchant into the local area of the thin layer without exposing a neighboring area adjacent to the local area of the thin layer to the etchant.

The shape profile generator preferably includes a light source for irradiating a light onto the exposed local area of the thin layer, a detector for detecting an intensity of light reflected from the exposed local area of the thin layer, and a comparing part for comparing the intensity of the light reflected from adjacent reflecting points of the exposed local area.

The shape profile generator preferably further includes a transformer for transforming the shape profile into an image.

The transformer preferably includes a solid state imaging device.

The solid state imaging device may be a charge-coupled device.

According to the embodiments of the present invention, a density profile of impurities included in a pattern of a semiconductor substrate may be monitored in real-time without causing destruction of the substrate during the patterning process. Furthermore, the monitored impurity density is backwardly fed into a controller to thereby control the amount of impurities used for forming the thin layer in real-time.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DESCRIPTION OF THE EXEMPLARY EMBODIMENTS

The present invention now will be described more fully hereinafter with reference to the accompanying drawings, in which exemplary embodiments of the present invention are shown.

Figure 1:
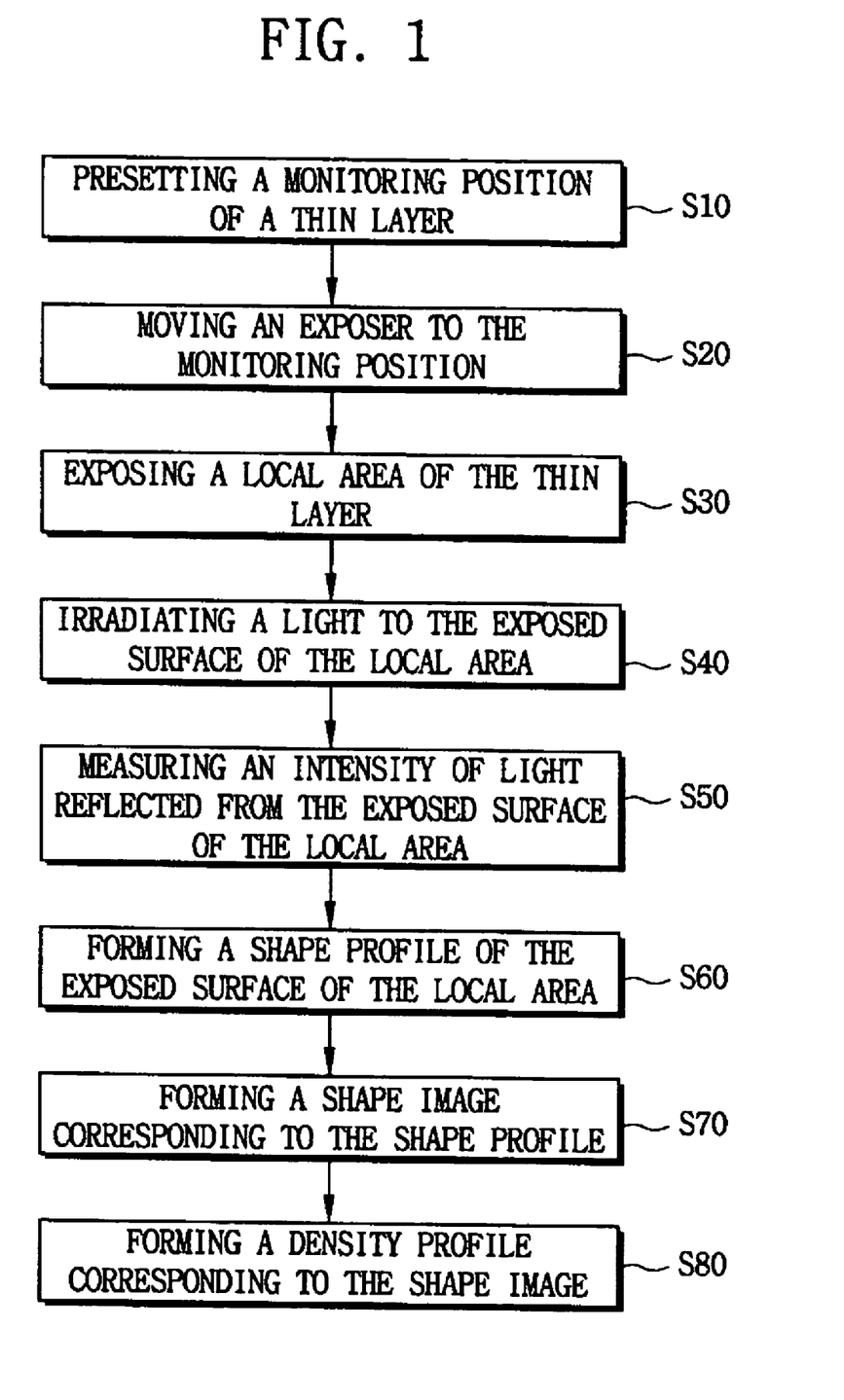
FIG. 1 is a flowchart for showing a method of monitoring the density profile of impurities according to an exemplary embodiment of the present invention.

FIG. 1 is a flowchart for showing a method of monitoring a density profile of impurities according to an exemplary embodiment of the present invention.

Referring to FIG. 1, a monitoring position of a thin layer is first preset in step S10. The thin layer is coated on a substrate, and includes a plurality of impurities. A density profile of the impurities is monitored from the monitoring position in a direction of a thickness of the thin layer. An amount of impurities injected into the thin layer during the patterning process may be varied according to processing conditions. Here, boron (B) and phosphorus (P) injected into an insulating interlayer such as a BPSG layer are described. A BPSG layer is coated on an entire surface of a substrate through an APCVD process, and an amount of triethyl borate $(B(OC_2H_5)_2$, hereinafter, referred to as TEB) and triethyl phosphine oxide $(PO(OC_2H_5)_3$, hereinafter, referred to as TEPO) during the APCVD process determines the amount of boron and phosphorus injected into the BPSG layer. Accordingly, a lower portion of the BPSG layer in which boron (B) and phosphorus (P) have already been deposited includes a predetermined density of boron (B) and phosphorus (P), so that an arbitrary position at the lower portion of the BPSG layer is selected as the monitoring position. As an exemplary embodiment, the BPSG layer disposed on an edge portion of the substrate or corresponding to a pattern to be monitored is selected for monitoring the density profile of the impurities.

An exposer for exposing a local area of the thin layer is moved to the monitoring position of the thin layer in step S20. A controller having information on the monitoring position controls the exposer to move to the monitoring position.

The local area of the thin layer is exposed in a direction of the thin layer thickness in step S30. For example, the local area is exposed through a wet etching process, and an etchant for the etching process is injected through a nozzle. The nozzle may be a micropipette or a probe having a diameter less than or equal to several micrometers, which are currently in wide use in electron microscopes, so that a neighboring area adjacent to the injected local area of the BPSG layer is not exposed. For example, the etchant may be a buffered oxide etchant (hereinafter, referred to as BOE) comprising about 28% $NH_4OH$, about 49% HF, and a residual of water. The local area of the BPSG layer may be over-etched, under-etched or normally etched depending on the density of boron (B) and phosphorus (P), so that a cross sectional surface of the local area is formed to be bulgy and hollow in the direction of the thickness of the BPSG layer corresponding to the density of the boron (B) and phosphorus (P). A light is irradiated into a plurality of reflecting points on the etched surface of the BPSG layer from a light source in step S40. The light is differently reflected from each of the reflecting points depending on ruggedness of the cross sectional surface of the BPSG layer. A detector detects the reflected light and measures the light intensity of the reflected light in step S50. The light source and detector form a position sensitive detector. When the light source and detector are fixed to an arbitrary position, the intensity of light that is reflected from the cross sectional surface and detected by the detector may be different in accordance with the ruggedness of the cross sectional surface due to the doppler effect, so that the light intensity of the reflected light indicates the prominence and depressions of the etched cross sectional surface. Accordingly, comparing the light intensity on the reflecting points adjacent with each other may create a shape profile showing the ruggedness of the cross sectional surface of the local area of the BPSG layer in step S60. For example, the light intensity of the reflected light may be transformed into a visual image, thus the shape profile may be visually verified as the image. A solid state imaging device, such as a charge-coupled device (CCD), may be used for transforming the light intensity into the visual image.

According to experimental results described in the following, an etching rate is correlated with the density of boron (B) and phosphorus (P) injected into the BPSG layer, thus the density of the boron (B) and the phosphorus (P) may be uniquely determined corresponding to the etching depth indicated in the shape profile or the shape image. Therefore, variation of the etching depth on the entire cross sectional surface of the BPSG layer corresponds to the variation of the density of the boron (B) and the phosphorus (P), so that the density profile of the boron (B) and the phosphorus (P) is obtained along the direction of the thickness of the BPSG layer in step S80.

As described above, the amount of TEB and TEPO gases determines the amount of boron (B) and phosphorus (P) injected into the BPSG layer during the APCVD process. Accordingly, the composition variation of the TEB and TEPO gases creates a split layer from which the density of the boron (B) and the phosphorus (P) is changed in the BPSG layer. The split layer may be created by a supply failure such as a chocking of a gas pipe as well as by intentional control of the amount of TEB and TEPO gases.

Figure 2A:
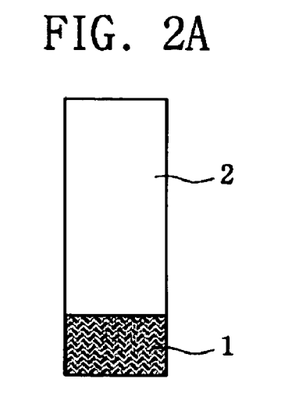
FIGS. 2A to 2C illustrate cross sectional views of experimental specimens each of which schematically illustrates a split layer dividing a phosphorus prominent region and a boron prominent region.
Figure 2B:
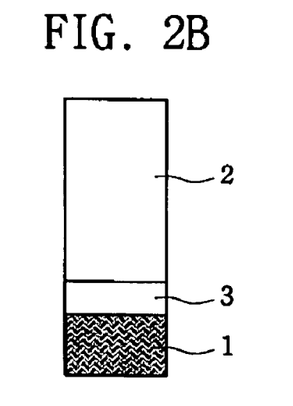
Figure 2C:
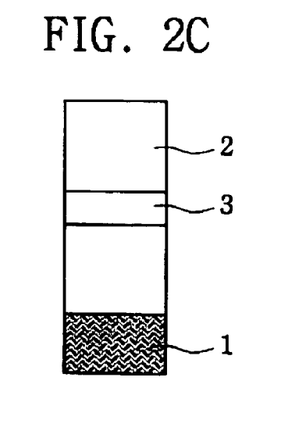

Three kinds of experiments on BPSG specimens were carried out for investigating a correlation between the shape of the etched surface and the density profile of the boron (B) and the phosphorus (P) in the BPSG layer. FIGS. 2A to 2C illustrate cross sectional views of experimental specimens, each of which schematically illustrates a split layer that divides a phosphorus prominent region and a boron prominent region.

Specimen I is a standard BPSG layer 2 on a substrate 1 including an allowable density profile of boron (B) and phosphorus (P), and includes no split layer, as shown in FIG. 2A. Specimen II, which is provided for investigating an effect of a split layer on an etching surface, includes a split layer 3 formed on a boundary portion between a BPSG layer 2 and a substrate 1, as shown in FIG. 2B. Specimen III includes a split layer 3 formed on a middle portion of a BPSG layer 2 on a substrate 1, as shown in FIG. 2C. Each of the specimens was split into various thin slices and wet-etched using a BOE solution for 90 seconds. Then, the etched surfaces of the slices were scanned with a scanning electron microscope (SEM).

Figure 3:
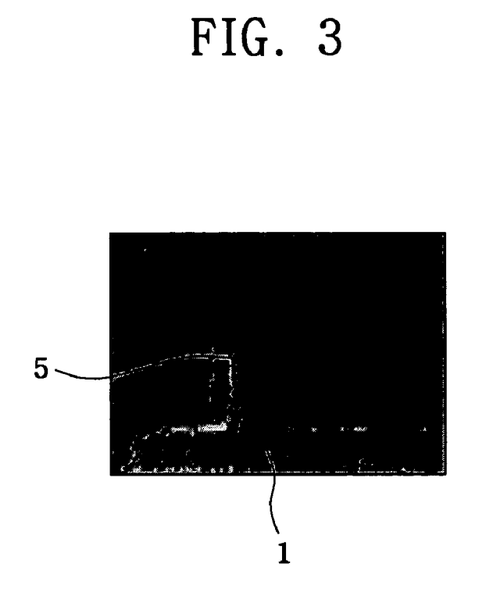
FIG. 3 is an image scanned by a scanning electron microscope (SEM) showing an etched surface of a specimen I.
Figure 4:
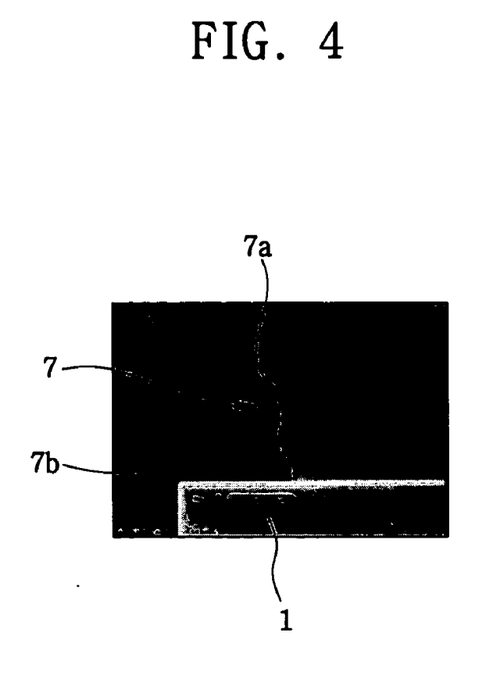
FIG. 4 is an image scanned by an SEM showing an etched surface of a specimen II.

FIG. 3 is an image scanned by the SEM showing an etched surface of specimen I. FIG. 4 is an image scanned by the SEM showing an etched surface of specimen II.

The etched surface 5 of the standard BPSG layer of specimen I is extremely smooth and has no ruggedness thereon, as shown in FIG. 3. However, the BPSG layer including the split layer 3 neighboring the substrate 1 of specimen II is etched away deeper than the standard BPSG layer, so that an etched surface 7 of the BPSG layer includes a first surface 7a perpendicular to the substrate 1 and a second surface 7b inclining to the substrate 1, as shown in FIG. 4. FIG. 4 also shows that the over-etched thickness of the second surface 7b is approximately identical to the thickness of the split layer 3. Accordingly, the density disparity of the boron (B) and the phosphorus (P) causes an etching rate difference, so that the etching depth differs on the etching surface. Therefore, the split layer was investigated on the etched surface.

To generalize the above-described experimental results on specimen II for investigating a correlation between a split layer and etching depth, eight experiments were carried out on specimen III while an amount of injected boron (B) and phosphorus (P) were varied. A split layer 3 was formed at an arbitrary position in specimen III. Table 1 shows the amounts of boron (B) and phosphorus (P) injected in each experiment. In Table 1, a (−) sign means that less boron (B) and phosphorus (P) were injected than an allowable amount for a standard BPSG layer and no sign means that more boron (B) and phosphorus (P) were injected than the allowable amount for a standard BPSG layer. TEPO and TEB gases were simultaneously supplied during the CVD processes, such that an amount of injected TEB gas was fixed when an amount of injected TEPO gas was varied, and an amount of injected TEPO gas was fixed when an amount of injected TEB gas was varied.

TABLE 1

| Number | Mass variation (ΔMgas) | | Weight percent of P | Weight percent of B | Thickness (Å) |
|---|---|---|---|---|---|
| 1 | TEPO | −30% | 5.79 | 3.44 | 5050.5 |
| 2 | | −10% | 5.98 | 3.15 | 5005.5 |
| 3 | | 10% | 6.03 | 3.18 | 5026.9 |
| 4 | | 30% | 6.07 | 3.18 | 5029.7 |

TABLE 1-continued

| Number | Mass variation (ΔMgas) | | Weight percent of P | Weight percent of B | Thickness (Å) |
|---|---|---|---|---|---|
| 5 | TEB | −30% | 5.85 | 3.26 | 5046.8 |
| 6 | | −10% | 5.81 | 3.50 | 5071.3 |
| 7 | | 10% | 5.87 | 3.51 | 5042.8 |
| 8 | | 30% | 6.10 | 3.34 | 5042.2 |

Figure 5A:
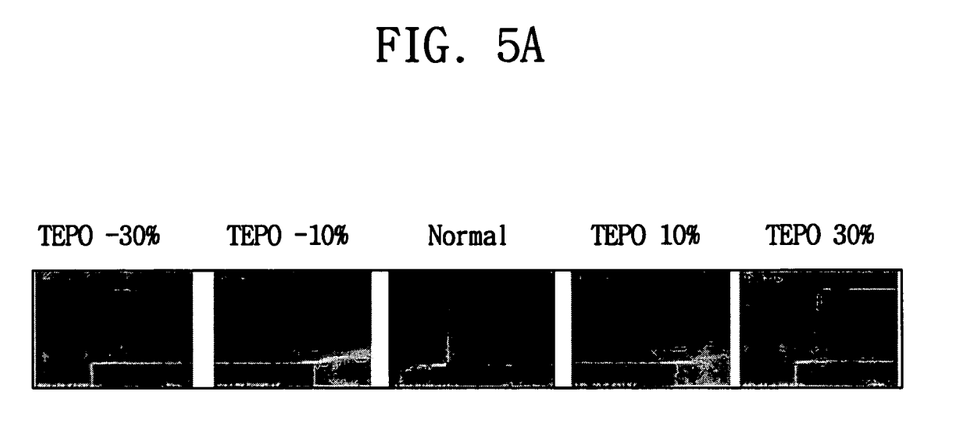
FIG. 5A illustrates images scanned by an SEM showing an etched surface of a BPSG layer when an injected amount of TEPO gas is varied.
Figure 5B:
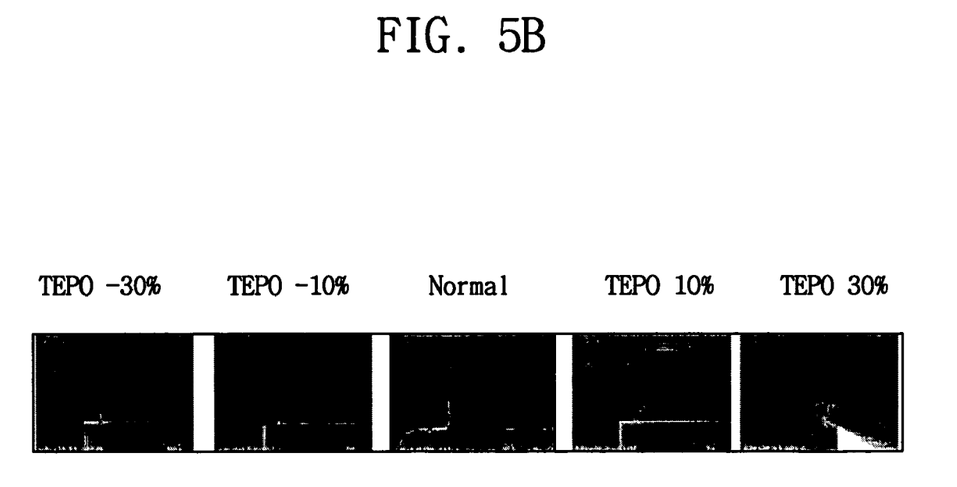
FIG. 5B illustrates images scanned by an SEM showing an etched surface of a BPSG layer when an injected amount of TEB gas is varied.

FIG. 5A shows SEM scanned images of etched surfaces of the BPSG layer when the amount of TEPO gas injected was varied, and FIG. 5B shown SEM scanned images of etched surfaces of the BPSG layer when the amount of TEB gas injected was varied. Figures indicated as "NORMAL" show SEM scanned images of etched surfaces of a standard BPSG layer including an allowable amount of boron (B) and phosphorus (P), i.e., when standard amounts of both TEPO and TEB gasses were injected.

FIGS. 5A and 5B indicate that a boundary layer is formed on an etched surface of a BPSG layer corresponding to a position of a split layer. Accordingly, referring to FIGS. 4, 5A and 5B, it is confirmed that a split layer between boron (B) and phosphorus (P) in a BPSG layer causes a shape change of an etched surface of the BPSG layer corresponding to the split layer regardless of the split layer position. Therefore, the shape change of the etched surface of the BPSG layer and the split layer in the BPSG layer correspond to each other one to one, so that the density profiles of the boron (B) and the phosphorus (P) in the BPSG layer may be deduced from an analysis of a shape image of an etched surface of the BPSG layer.

In addition, comparing FIG. 5A with FIG. 5B indicates that a shortage or surplus of boron (B) and phosphorus (P) greatly effects an etching depth of a surface of a BPSG layer. The etching depth is deeper when less than 30% or more than 30% of the allowable quantity of TEPO gas is supplied than when the quantity of TEPO gas supplied is varied by only as much as ±10% of the allowable quantity. Similarly, the etching depth on condition that less than 30% or more than 30% of the allowable quantity of TEB gas is supplied is deeper than when the amount of TEB gas supplied is varied by only as much as much as ±10% of the allowable quantity. Accordingly, an etching depth of an etched surface of a BPSG layer has a direct correlation with an injected amount of boron (B) and phosphorus (P). Although the experiment is carried out on conditions that the TEPO and TEB gases are supplied by more or less then as much as 30% and 10% of the allowable quantities, many iterated experiments under conditions in which the TEPO and TEB gases are varied by much less gives continuous one-to-one correspondence between the etching depth and the injected amount of the boron (B) and the phosphorus (P). In addition, FIGS. 5A and 5B also indicate that the BPSG layer is under etched when less than allowable amounts of boron (B) and phosphorus (P) are supplied, and the BPSG layer is over etched when more than allowable amounts of boron (B) and phosphorus (P) are supplied. The above experimental results schematically show the correlation between etching depth of a BPSG layer and an injected amount of boron (B) and phosphorus (P). However, the correlation is more apparent when experimental conditions are more sufficiently satisfied.

According to the experimental results, a density profile of boron (B) and phosphorus (P) may be deduced from analysis of a surface shape of an etched surface of a BPSG layer. Furthermore, the density profile may be monitored by comparing the density profile with a database of the correlation between etching depth and injected amounts of boron (B) and phosphorus (P).

Figure 6:
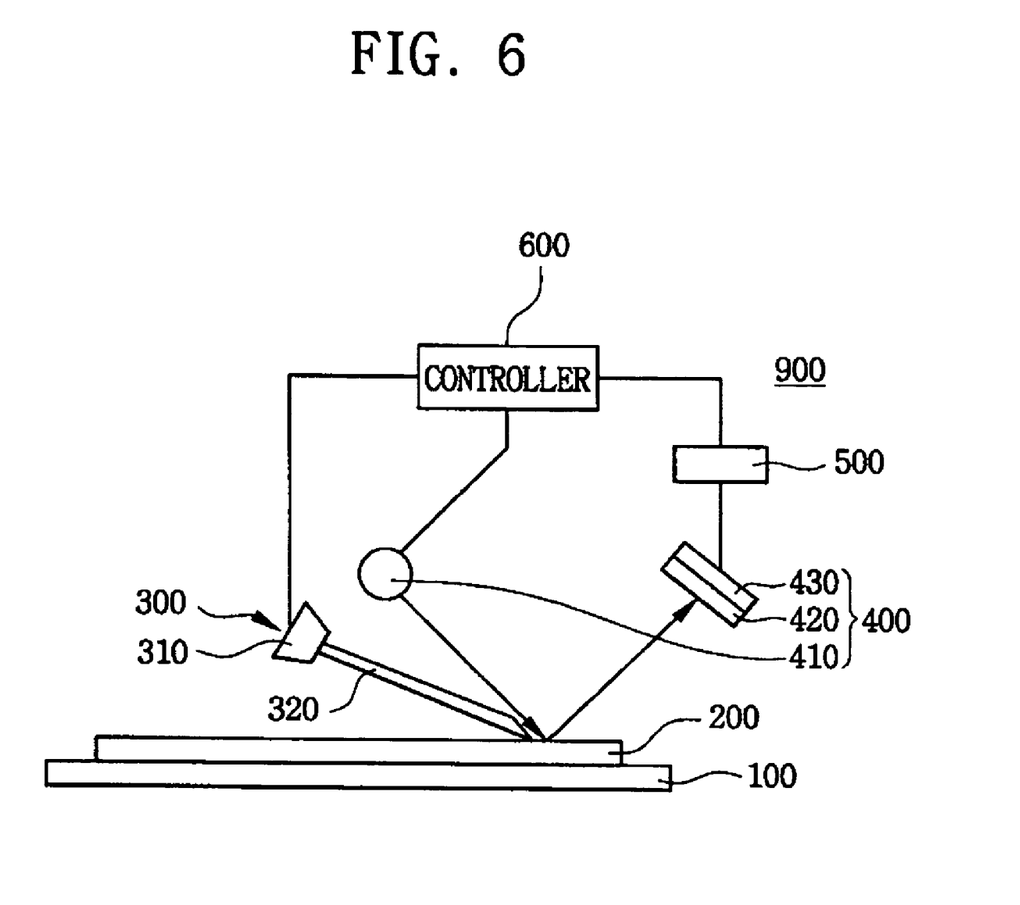
FIG. 6 illustrates a structural view depicting an apparatus for monitoring a density profile of impurities according to an exemplary embodiment of the invention.

FIG. 6 illustrates a structural view showing a monitoring apparatus for monitoring a density profile of impurities according to an exemplary embodiment of the present invention.

Referring to FIG. 6, the monitoring apparatus 900 includes a stage 100 on which a substrate 200 including a thin layer is disposed, an exposer 300 for exposing a local area of a thin layer, a shape profile generator 400 for generating a shape profile of the exposed local area, a density profile generator 500 for generating a density profile of impurities of the thin layer, a controller 600 for controlling the exposer 300, the shape profile generator 400, and the density profile generator 500.

For example, the stage 100 may be formed of a flat plane, and the substrate 200 may be disposed on the stage 100. A thin layer including a plurality of impurities is coated on the substrate 200. The thin layer may be a BPSG layer, which is a kind of insulating interlayer, including a plurality of boron (B) and phosphorus (P). While the exposer 300 and the shape profile generator 400 move to a predetermined position on the BPSG layer, the stage may move corresponding to the exposer 300.

The exposer 300 includes a container 310 for containing an exposing material and a nozzle 320 for injecting the exposing material into a local area of the BPSG layer. If the exposer 300 exposes the local area of the BPSG layer through a wet-etching process, then the container 310 is formed of a chemical-resistant tube for an etching solution such as a buffer oxide etchant (BOE). The nozzle 320 may be a micropipette or a probe having a diameter less than or equal to several micrometers, which is currently in wide use in scanning electron microscopes, so that a neighboring area adjacent to the injected local area of the BPSG layer is not exposed. That is, the etching process may be locally carried out to thereby expose the local area of the substrate along a direction of thickness of the BPSG layer without destructing the substrate.

The shape profile generator 400 includes a light source 410 for irradiating a light to the exposed local area of the BPSG layer, a detector 420 for detecting a light intensity of a light reflected from the exposed local area of the BPSG layer, and a comparing part 430 for comparing the light intensity of light reflected from adjacent points of the exposed local area of the BPSG layer. A light is irradiated to the exposed local area of the BPSG layer from the light source 410, and is reflected from the exposed local area. Then, the reflected light is detected by the detector 420. As an example, the light source 410 and the detector 420 may integrally constitute a position sensitive detector (PSD). Comparing an intensity of the reflected light reveals an interval between the reflecting points of the exposed local area due to the Doppler effect. Therefore, the comparing part 430 compares the intensity of the light reflected from adjacent reflecting points over the entire surface of the local area, so that a shape profile over the exposed surface of the local area is formed. Prominent and depressed portions of the exposed surface of the local area may be verified from the shape profile. The shape profile generator 400 may further include a transformer for transforming the shape profile into an image. For example, the transformer may be a solid state imaging device such as a charge-coupled device (CCD). The conventional SEM apparatus may also be used for transforming the shape profile into an image, as would be known to one of ordinary skill in the art.

Since the etching depth on the surface of the BPSG layer corresponds to the densities of boron (B) and phosphorus (P) injected thereto, the density profile generator 500 generates a density profile of the boron (B) and phosphorus (P) injected into the BPSG layer corresponding to the prominences and depressions of the exposed surface of the local area along the direction of the thickness of the BPSG layer.

The controller 600 is electrically connected to the exposer 300, shape profile generator 400 and density profile generator 500, and controls the exposer 300, shape profile generator 400 and density profile generator 500 for systematic operation.

According to the present invention, only a local area of a thin layer coated on a semiconductor substrate is exposed, and a shape profile of the exposed local area is formed. Thus, the density of impurities in the thin layer may be generated. Therefore, a density profile may be generated without destroying the semiconductor substrate on which the thin layer is coated. Further, because only a local area of the thin layer coated on the semiconductor substrate is exposed, accuracy of analysis for measuring the density profile may be improved. In addition, the density profile of impurities included in the thin layer can be generated in real-time during a deposition process for coating the thin layer, so that even a local variation of the impurity density can be controlled in real-time during the deposition process.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of monitoring a density profile of impurities, the method comprising:
   presetting a monitoring position of a thin layer coated on a substrate, the density profile of impurities being monitored from the monitoring position in a direction of thickness of the thin layer;
   moving an exposer for exposing a local area of the thin layer to the monitoring position;
   exposing the local area of the thin layer along the direction of thickness of the thin layer;
   forming a shape profile of the exposed local area of the thin layer; and
   monitoring the density profile of impurities by determining a density of impurities in accordance with the shape profile,
   wherein the exposer is a device for performing an etching process, the exposer delivering an etchant to the local area, and
   exposing the local area includes delivering the etchant to the local area using the exposer, the etchant flowing through a tip of the exposer, the tip having a diameter of less than or equal to several micrometers.

2. The method as claimed in claim 1, wherein the thin layer includes an insulating interlayer coated on a semiconductor substrate.

3. The method as claimed in claim 2, wherein the insulating interlayer includes a borophosphorous silicate glass (BPSG) layer.

4. The method as claimed in claim 1, wherein exposing the local area of the thin layer along the direction of thickness of the thin layer comprises a wet etching process.

5. The method as claimed in claim 4, wherein the wet etching process is carried out using a buffer oxide etchant (BOE).

6. A method of monitoring a density profile of impurities, the method comprising:
   presetting a monitoring position of a thin layer coated on a substrate, the density profile of impurities being monitored from the monitoring position in a direction of thickness of the thin layer;

moving an exposer for exposing a local area of the thin layer to the monitoring position;

exposing the local area of the thin layer along the direction of thickness of the thin layer;

forming a shape profile of the exposed local area of the thin layer; and monitoring the density profile of impurities by determining a density of impurities in accordance with the shape profile, wherein forming the shape profile comprises:

irradiating a light onto the exposed local area of the thin layer;

detecting an intensity of the light reflected from the exposed local area of the thin layer; and comparing the intensity of the light reflected from adjacent reflecting points of the exposed local area.

7. The method as claimed in claim 6, wherein forming the shape profile further comprises transforming the shape profile into an image.

8. The method as claimed in claim 7, wherein transforming the shape profile into an image comprises using a solid state imaging device.

9. The method as claimed in claim 1, wherein exposing the local area of the thin layer along the direction of thickness of the thin layer comprises an etching process, and
the etching process causes a cross sectional surface of the exposed local area to vary when densities of the impurities vary.

10. The method as claimed in claim 9, wherein the etching process etches the local area along a second direction, the second direction perpendicular to the thickness of the thin layer, and
an etching depth in the second direction varies according to a shortage or surplus of the impurities in the local area.

11. The method as claimed in claim 1, wherein exposing the local area of the thin layer along the direction of thickness of the thin layer comprises an etching process,
the thin layer includes a first region and a second region, the second region corresponding to a split layer, and
the etching process etches the first and second regions at different rates.

12. The method as claimed in claim 1, wherein the shape profile exhibits variations in a second direction when densities of the impurities vary, the second direction perpendicular to the direction of the thickness of the thin layer.

13. A method of determining the presence of an impurity density boundary in a thin layer, comprising:

providing a substrate having the thin layer disposed thereon, the thin layer extending in a first direction substantially parallel to a major surface of the substrate;

removing a portion of the thin layer to expose a cross section of the thin layer, the cross section extending in a second direction perpendicular to the first direction; and analyzing the cross section of the thin layer, wherein analyzing the cross section of the thin layer includes:
reflecting light from the cross section,
determining an intensity of the reflected light, and
determining whether the impurity density boundary is present based on the intensity of the reflected light.

14. The method as claimed in claim 13, wherein removing the portion of the thin layer includes an etching process, and the presence of the impurity density boundary in the thin layer affects an etching rate of the etching process on adjacent sides of the impurity density boundary.

15. The method as claimed in claim 14, wherein the etching process etches the thin layer in the first direction at a rate that is dependent on an impurity density.

16. The method as claimed in claim 13, wherein the thin layer is a BPSG layer and the impurity density boundary is at least one of a boron density boundary and a phosphorus density boundary.

17. The method as claimed in claim 16, wherein the impurity density boundary corresponds to a split layer.

18. A method of monitoring a density profile of impurities, the method comprising:

presetting a monitoring position of a thin layer coated on a substrate, the density profile of impurities being monitored from the monitoring position in a direction of thickness of the thin layer;

moving an exposer for exposing a local area of the thin layer to the monitoring position;

exposing the local area of the thin layer along the direction of thickness of the thin layer;

forming a shape profile of the exposed local area of the thin layer; and monitoring the density profile of impurities by determining a density of impurities in accordance with the shape profile, wherein moving the exposer includes using a control device to move the exposer to the monitoring position.

19. A method of monitoring a density profile of impurities, the method comprising:

presetting a monitoring position of a thin layer coated on a substrate, the density profile of impurities being monitored from the monitoring position in a direction of thickness of the thin layer;

moving an exposer for exposing a local area of the thin layer to the monitoring position;

exposing the local area of the thin layer along the direction of thickness of the thin layer;

forming a shape profile of the exposed local area of the thin layer; and monitoring the density profile of impurities by determining a density of impurities in accordance with the shape profile, wherein exposing the local area includes etching the local area without cleaving the substrate.

20. A method of monitoring a density profile of impurities, the method comprising:

presetting a monitoring position of a thin layer coated on a substrate, the density profile of impurities being monitored from the monitoring position in a direction of thickness of the thin layer;

moving an exposer for exposing a local area of the thin layer to the monitoring position;

exposing the local area of the thin layer along the direction of thickness of the thin layer;

forming a shape profile of the exposed local area of the thin layer; and monitoring the density profile of impurities by determining a density of impurities in accordance with the shape profile, further comprising outputting the monitored density profile to an impurity doping system in real-time.

* * * * *